United States Patent [19]
Cincotta et al.

[11] Patent Number: 5,714,519
[45] Date of Patent: Feb. 3, 1998

[54] METHOD FOR REGULATING GLUCOSE METABOLISM

[75] Inventors: Anthony H. Cincotta, Charlestown, Mass.; Albert H. Meier, Baton Rouge, La.; John M. Wilson, Charlestown, Mass.

[73] Assignees: Ergo Science Incorporated, Wakefield, R.I.; The Board of Supervisors of Louisiana State University and Agricultural and Mechanical College, Baton Rouge, La.

[21] Appl. No.: 486,189

[22] Filed: Jun. 7, 1995

[51] Int. Cl.$^6$ .................................................. A61K 31/16
[52] U.S. Cl. .......................... 514/616; 514/665; 514/866
[58] Field of Search .................................. 514/616, 665, 514/866

[56] References Cited

U.S. PATENT DOCUMENTS

| | | | |
|---|---|---|---|
| 4,657,932 | 4/1987 | Martin et al. | 514/665 |
| 4,659,715 | 4/1987 | Meier et al. | |
| 4,749,709 | 6/1988 | Meier et al. | |
| 4,783,469 | 11/1988 | Meier et al. | |
| 5,006,526 | 4/1991 | Meier et al. | |

FOREIGN PATENT DOCUMENTS 2192541  7/1988  United Kingdom.

OTHER PUBLICATIONS

DiPiro et al., "Pharmacotherapy: A Pathophysiologic Approach", Elsevier, New York, New York (1989), pp., 307 and 818–819.
WPIDS Abstract 81-74700D [41], Daiichi Seiyaku Co. (1989).
Medline Abstract 88077245, Wittwer, C.T. et al. (1987).
Barnett, *Post Graduate Medical J.* 56:11–14, 1980.
Burns et al., *Chronopharmacology and Chronotherapeutics, Intl. Symp. on Chronopharm. and Chronother.*, Florida A&M Univ. pp. 315–381, 1978.
Cincotta et al., *J. Endocrinol.* 106:173–176, 1985.
Cincotta et al., *Ann. Notr. Metab* 33:305–314, 1989.
Cincotta et al., *Experientia* 43:416–417, 1987.
Eiseman, *J. Animal Science* 59:86–94, 1984.
Eiseman, *J. Animal Science* 59:95–104, 1984.
Emata et al., *J. Exp. Zool.* 233:29–34, 1985.
Harel et al., *Proc. La. Acad. of Sci.* 38:125, 1975.
Joseph et al., *Proc. Soc. Exp. Biol. Med.* 146:1150–1155, 1974.
Komorowski et al., *Aliment. Nutr. Metab.* 1(4):293, 1980.
Larsson et al., *La Kartidningen (Sweden)* 82(50):4425, 293, 1985.
Martin et al., *The Condor* 75:369–374, 1973.
Martin et al., *Chronobiology*, "Hormonal Control of Orientation in the White-Throated Sparrow, *Zonotrichia Albicollis*." pp.641–646, 1974.
Martin et al., *Proc. La. Acad. of Sci.* 38:127, 1975.
Martin et al., *Am. Zoologist* 18(3):672, 1978.
Martin, D., "Hormonal Regulation of Migratory Orientation in the White–Throated Sparrow, *Zonotrichia Albicollis*." Diss. LSU, 1974.
Martin, D., "Factors Influencing the Circadian Rhythm of Locomotor Activity in the Anabatoid Fish, *Tirchogaster Trichopterus Sumatramus*." Thesis. Sam Houston State College, 1969.
Meier et al., *Gen & Comp. Endocrinol. Supp* 3:499–508, 1972.
Meier et al., *Gen & Comp. Endocrinol.* 26:253–258, 1975.
Meier et al., *Current Ornithology* 2:303–343, 1984.
Meier et al., *Experientia* 48:248–253, 1992.
Meier et al., *Gen & Comp. Endocrinol.* 17:311–318, 1971.
Meier et al., *Proc. Soc. Exp. Biol. & Med.* 137:408–415, 1971.
Meier et al., *Science* 173:1240–1242, 1971.
Meier et al., *Physiol. Zool.* 41(1):95–103, 1968.
Southern et al., *J. Anim. Sci*, 68931–936, 1990.
Wilson et al., *Chronobio Int.* 6:113–121, 1989.
Kodama, J. et al. (1990) Effect of Captopril on Glucose Concentration *Diabetes Care* 13:1109–1111.
Torlone, E. et al. (1991) ACE–inhibition increases hepatic and extrahepatic sensitivity to insulin in patients with Type 2 (non–insulin–dependent) diabetes mellitus and arterial hypertension *Diabetologia* 34:199–125.
Paolisso, G. et al. (1992) ACE–inhibition improves insulin–sensitivity in aged insulin–resistant hypertensive patients *Journal of Human Hypertension* 6:175–179.
Rett, K. et al. (1986) Angiotensin converting enzyme inhibitors in diabetes: experimental and human experience *Postgraduate Medical Journal* 62(Supp. 1):59–64.
Palatini, P. et al. (1989) Inhibition of dopamine beta–hydroxylase by captopril *Biochemical Pharmacology* 38:1011–1013.

*Primary Examiner*—Marianne M. Cintins
*Assistant Examiner*—M. Moezie
*Attorney, Agent, or Firm*—Darby & Darby

[57] ABSTRACT

This invention relates to a method for modifying metabolism in a vertebrate animal which entails the administration of pantethine or cysteamine at a predetermined time daily. The method is useful in the treatment of hyperglycemia, glucose intolerance, insulin resistance, and hyperinsulinemia.

27 Claims, 1 Drawing Sheet

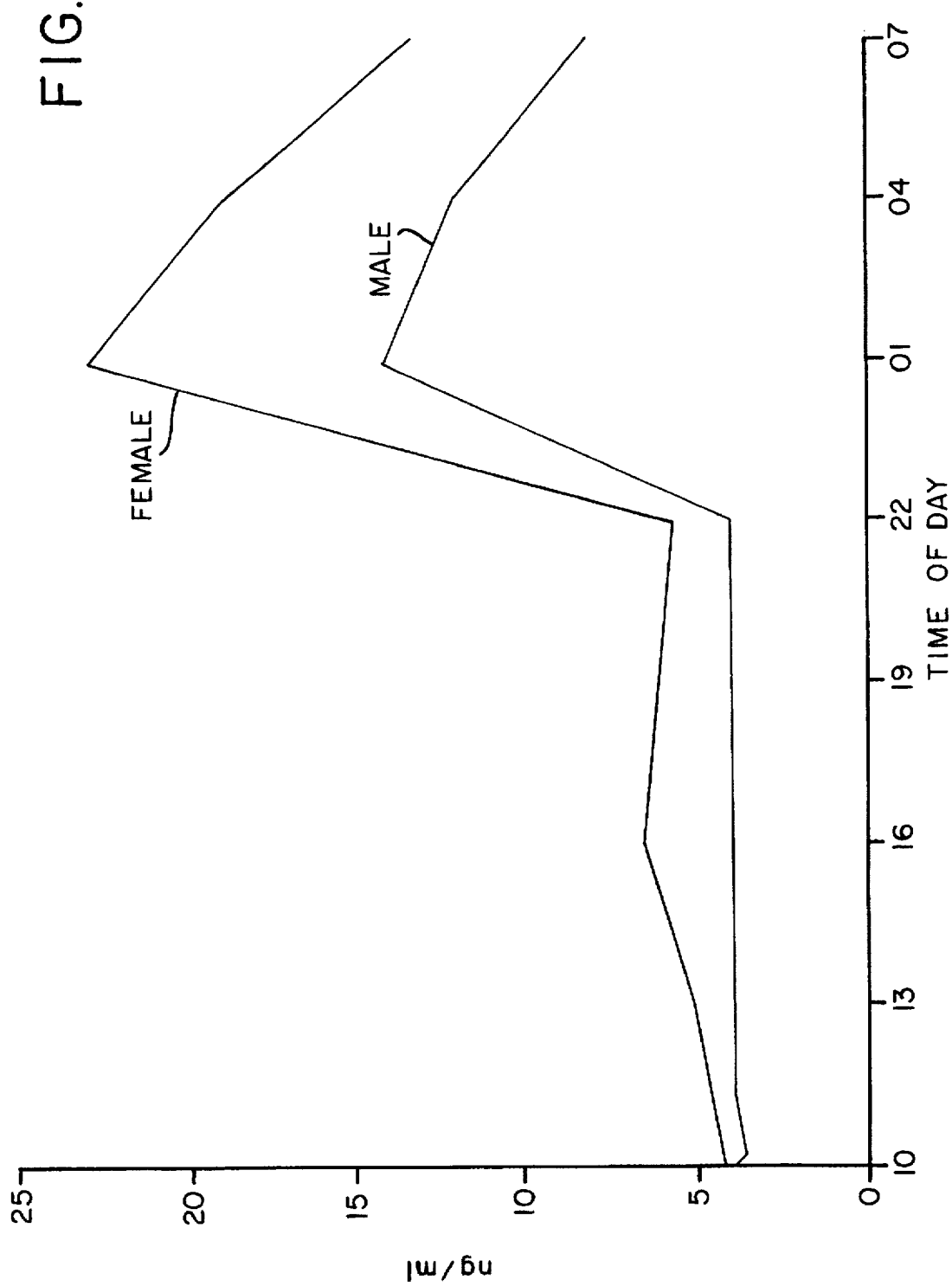

METHOD FOR REGULATING GLUCOSE METABOLISM

FIELD OF THE INVENTION

This invention pertains to methods for regulating or ameliorating metabolic defects. This invention, further, relates to methods for reducing in a subject, such as a vertebrate animal (including a human), at least one of the following indices of metabolism: insulin resistance, hyperinsulinemia, hyperglycemia, and body fat stores. More generally, the invention pertains to improvement of glucose and insulin metabolism disorders, especially those associated with Type II diabetes. The method of the invention comprises administration or timed administration (i.e. administration at a predetermined time within a 24-hour period) of pantethine or cysteamine to a subject in need of such treatment.

BACKGROUND OF THE INVENTION

DIABETES

Diabetes, one of the most insidious of the major diseases, can strike suddenly or lie undiagnosed for years while attacking the blood vessels and nerves. Diabetics, as a group, are far more often afflicted with blindness, heart disease, stroke, kidney disease, hearing loss, gangrene and impotence. One third of all visits to physicians are occasioned by this disease and its complications. Diabetes and its complications are a leading cause of premature death in the United States and in the Western world.

Diabetes adversely affects the way the body uses sugars and starches which, during digestion, are converted into glucose. Insulin, a hormone produced by the pancreas, makes the glucose available to the body's cells for energy. In muscle, adipose (fat) and connective tissues, insulin facilitates the entry of glucose into the cells by an action on the cell membranes. In the liver the ingested glucose is normally converted to $CO_2$ and $H_2O$ (50%); to glycogen (5%); and to fat (30–40%), the latter being stored as fat deposits. Fatty acids from the adipose tissues are circulated, returned to the liver for re-synthesis of triacylglycerol and metabolized to ketone bodies for utilization by the tissues. The fatty acids are also metabolized by other organs.

The net effect of insulin is to promote the storage and use of carbohydrates, protein and fat. Insulin deficiency is a common and serious pathologic condition in humans. In insulin-dependent (IDDM or Type I) diabetes, wherein the pancreas produces little or no insulin, insulin must be injected daily. In noninsulin-dependent (NIDDM or Type II) diabetes the pancreas retains the ability to produce insulin, in fact it may produce higher than normal amounts of insulin (hyperinsulinemia), but due to a cellular resistance to insulin, the amount of insulin is relatively insufficient. Insulin resistance can be defined as a state in which a normal amount of insulin produces a subnormal biologic (metabolic) response. In insulin-treated patients with diabetes, insulin resistance is considered to be present whenever the therapeutic dose of insulin exceeds the secretory rate of insulin in normal persons. Insulin resistance is also associated with hyperinsulinemia when normal or elevated levels of blood glucose are co-present.

Either type of diabetes causes widespread metabolic abnormalities. In most NIDDM subjects, the metabolic abnormalities associated with NIDDM are (1) reduced entry of glucose into various "peripheral" tissues and (2) increased liberation of glucose into the circulation from the liver. Thus, there is an excess of extracellular glucose and a deficiency of intracellular glucose. Elevated blood lipids and lipoproteins are a further common complication of diabetes. The cumulative effect of these diabetes-associated abnormalities is severe damage to blood vessels and nerves.

There is, currently, no effective treatment for controlling either hyperinsulinemia or insulin resistance, except for certain work by the present inventors as follows:

PREVIOUS WORK OF THE PRESENT INVENTORS

The present inventors and their co-workers have found that administration of certain prolactin inhibitors (e.g., dopamine agonists such as bromocriptine) and/or prolactin stimulators (e.g., dopamine antagonists, such as metoclopramide; serotonin agonists and precursors, such as 5-hydroxytryptophan) and particularly administration of such substances at predetermined times, reduce body fat stores, obesity, plasma triglycerides and cholesterol and insulin resistance: U.S. Pat. Nos. 4,659,715; 4,749,709; 4,783,469; 5,006,526 5,344,832 and PCT Application U.S. 92/11166.

RELATED APPLICATIONS

Co-pending patent application Ser. No. 07/192,332 (now abandoned in favor of its Rule 62 continuation Ser. No. 07/919,685 now U.S. Pat. No. 5,316,793) discloses methods for regulating lipid metabolism disorders by administering prolactin (or both prolactin and a glucocorticosteroid ("GC")) into the bloodstream of an animal or human on a timed daily basis in an amount and for a period of time sufficient to increase insulin sensitivity.

The prolactin (or prolactin and glucocorticosteroid—"GC") injections are timed to create a peak in the subject's daily prolactin (or both prolactin and glucocorticosteroid) level profile that coincides in time with the peak prolactin level (or with both prolactin and GC peaks, respectively) of a lean, insulin-sensitive human in order to increase insulin sensitivity and reduce body fat stores. Alternatively, injections of the same agent(s) are timed towards the peak prolactin level time of an obese subject to achieve fat gain in a lean subject, if desired.

Co-pending application Ser. No. 07/463,327 (now abandoned in favor of its Rule 62 continuation Ser. No. 08/249, 808 now U.S. Pat. No. 5,555,623 which is a continuation of Ser. No. 07/719,745, now U.S. Pat. No. 5,344,832) discloses a method of modifying and resetting prolactin and GC rhythms in an obese animal by administering a dopamine agonist at a predetermined time of day such that the prolactin (and/or GC) peak(s) of the obese animal will be phase-shifted to coincide with those of a lean animal. This results in the reduction of at least one of the following: body fat stores, body weight, hyperinsulinemia, hyperglycemia and the increase of insulin sensitivity.

In co-pending application Ser. No. 07/719,745 (now U.S. Pat. No. 5,344,832) discloses and claims enhanced methods for modifying and resetting the phase as well as the amplitude of prolactin daily rhythms. These methods comprise both (a) administering to the subject a dopamine agonist just after the time at which the normal prolactin profile peaks to reduce prolactin levels to the low "day" levels and (b) administering to the subject a prolactin stimulator at a time before the prolactin level peaks in normal subjects to achieve or maintain a peak for prolactin at night-time. The objective of this treatment is alteration of the subject's prolactin secretion profile to mimic in shape and time the profile of a lean healthy human not suffering from one or more of these metabolic disorders.

U.S. Pat. No. 5,344,832 also discloses and claims the further administration of a thyroid hormone to subjects that are being treated with a dopamine agonist and prolactin stimulator, especially to those subjects that are chronically or seasonally hypothyroid.

Co-pending applications Ser. No. 07/995,292 now U.S. Pat. No. 5,585,347 (which is a continuation-in-part of U.S. application Ser. No. 07/719,745, now U.S. Pat. No. 5,344,832) and Ser. No. 08/264,558 now abandoned (which is a continuation-in-part of U.S. application Ser. Nos. 07/995,292 now U.S. Pat. No. 5,585,347, 08/178,569 now pending and 08/171,897 now abandoned) discloses methods for determining whether the daily circulating prolactin profile in a subject is abnormal, and methods for normalizing prolactin profiles found to be aberrant. In pertinent part, the treatment method involves administration of a prolactin inhibitor no later than the time at which, during waking hours, the prolactin level in the subject is at its highest. The method may also involve administration of a prolactin stimulator timed to cause a peak of prolactin level to occur during night-time. The objective of this treatment is alteration ("sculpting") of the subject's prolactin profile to mimic or approach in shape and time the profile of a lean healthy human not suffering from any disorders.

Co-pending patent application Ser. No. 08/263,607 now pending; continuation-in-part of co-pending application Ser. No. 07/995,292 now U.S. Pat. No. 5,585,347, which is itself a continuation-in-part of Ser. No. 07/719,745 (now U.S. Pat. No. 5,344,832), discloses methods for regulating lipid and glucose metabolism by the timed administration of pirenzepine, methyl scopolamine or another muscarinic (preferably M1) receptor antagonist alone or in combination with a prolactin inhibitor as a treatment for diabetes, particularly Type II diabetes, and more generally glucose metabolism disorders that are associated with Type II diabetes generally lipid metabolism disorders. This application further discloses maintaining therapy for a sufficient period of time to cause a resetting of the treated subject's prolactin daily rhythm resulting in continuing metabolic improvement after the cessation of therapy.

Co-pending patent application Ser. No. 08/271,881 now pending discloses method of adjusting the phase relationship between the circadian rhythms for prolactin and for one or more immune responses. The invention involves normalizing (or resetting) the circadian rhythm for prolactin of a subject in need of such treatment to resemble that of a young healthy subject. The invention, further, involves adjusting the prolactin circadian rhythm so that its phase and amplitude correlate with the immunologic responsiveness to prolactin thus exerting an amplifying effect on a predetermined aspect of the immune response.

OBJECTS OF THE INVENTION

The present invention has as its objects to improve metabolic indices of vertebrate mammals, including humans, by ameliorating one or more abnormal metabolic parameters such as those associated with diabetes.

A specific object of the invention is to correct abnormalities in the glucose metabolism of a vertebrate animal, including humans, by administering an effective amount for: decreasing glucose intolerance; decreasing hyperinsulinemia; decreasing insulin resistance; and/or decreasing hyperglycemia of pantethine or cysteamine.

A further object of the invention is a method for treating diabetes in a vertebrate animal, including a human, by administering, preferably at a predetermined time, an effective amount for reducing hyperinsulinemia, decreasing insulin resistance, and decreasing hyperglycemia of pantethine or cysteamine.

A still further object of the invention is a method for reducing body fat levels by administering pantethine or cysteamine at timed intervals.

A still further object of the invention is continuing the administration of pantethine for a predetermined time period to reset the central neural oscillators (e.g. those expressed by the circadian rhythm of circulating prolactin) such that their phase and amplitude (e.g. the phase and amplitude of the prolactin rhythm) approaches that of a lean and healthy subject of the same species (and where applicable sex), this effect persisting even after the cessation of the administration of the pantethine.

BRIEF DESCRIPTION OF THE DRAWING

FIG. 1 depicts the standard prolactin profile for healthy young humans in terms of average prolactin values (ng/ml) vs time of day in hours. M=standard prolactin profile for males; F=standard prolactin profile for females.

SUMMARY OF THE INVENTION

The foregoing objects are accomplished by administering pantethine to a vertebrate subject in need of such treatment in an effective amount to reduce or ameliorate one or more aberrant indices associated with metabolism disorders (e.g., reducing glucose intolerance, reducing insulin resistance, reducing hyperglycemia, reducing hyperinsulinemia, ameliorating or treating Type II diabetes, and reducing levels of body fat).

Preferably, pantethine is administered at a predetermined time ("timed administration") during a 24-hour period to augment its beneficial effect.

Continuing the timed therapy referred to above for a period of time stabilizes these improvements and often causes them to persist after cessation of the treatment. Persistence and stabilization of these improvements and resetting of circadian rhythms is referred to as the "indirect effect" or "long-term effect" of pantethine (alone or in combination with prolactin inhibitors), and is attributed to resetting of a hypothalamic metabolistat expressed by way of circadian rhythms, more specifically prolactin rhythms and neural phase oscillators in the central nervous system. These effects can persist on a long-term basis after cessation of treatment.

DETAILED DESCRIPTION OF THE PREFERRED EMBODIMENTS

All patents, patent applications and literature references cited herein are incorporated by reference in their entirety as if their disclosures were physically present in the present specification. In case of conflict, however, the present disclosure controls.

Vertebrate animals include without limitation humans, other mammals (e.g. domestic animals, laboratory animals and pets) and birds.

TIMED ADMINISTRATION FOR ALTERING METABOLISM

The direct effect of pantethine in accomplishing one or more of the following: decreasing hyperglycemia, decreasing glucose intolerance, decreasing insulin resistance and decreasing hyperinsulinemia can be effected by administering to a vertebrate animal in need of such treatment from about 15 to about 500 mg/kg of body weight per day and preferably 20 to 350 mg/kg of body weight per day of pantethine.

The general pantethine dose range (i.e. the effective amount for reducing insulin resistance, hyperinsulinemia and hyperglycemia, and for treating diabetes) is between about 15 to about 500 mg/kg of body weight per day. The preferred dose is between about 20 to 350 mg/kg of body weight per day of pantethine. The maximum dose of pantethine in humans is anticipated at about 25 g/patient/day. It is expected that the amount of pantethine will be subject to optimization but that this will involve no more than routine experimentation.

It is also possible to employ cysteamine, a pantethine metabolite, in practicing the method of the invention. When cysteamine is used, the effective dose for regulating glucose metabolism is between about 1.0 to about 300 mg/kg of body weight per day and preferably between about 5 and about 150 mg/kg of body weight per day. The maximum daily dose of cysteamine is about 5 grams.

It is preferred that pantethine be administered at a predetermined time during a 24-hour period designed to reduce hyperglycemia most preferably at the beginning of the subject's daily activity period. Alternatively it is preferred that pantethine be administered at a predetermined time during a 24 hour period to reduce lipogenesis during a daily lipogenic interval when most fat is synthesized. The interval is determined indirectly by measuring one or more plasma lipid values, preferably VLDL values at several (e.g. 3 or 4) spaced-apart times within all or a portion of a 24 hour period and determining the interval when the circulating VLDL increases, reaches a maximum and then begins to decline. In general, the interval of increased lipogenesis precedes in phase the interval of increased VLDL and occurs during the latter half of the subject's daily activity period (for humans, usually in early evening). However, it is preferred to make the aforedescribed measurements, rather than rely on the general rule because of the possible shifts of this interval in subjects in need of treatment.

For example, pantethine might be administered about 6–12 hours before the increase in VLDL values, or at the beginning of the daily activity/wakefulness period. Because timing of the administration will vary with the species to be treated (diurnal/nocturnal) and dosage of the pantethine, the foregoing 6–12 hour interval can serve as a guideline for more precise determinations. Effectiveness of the administration at a particular time is assessed by such indices as glucose level, insulin level, insulin sensitivity or glycosylated hemoglobin.

In more detail, a preferred effective time for administering pantethine is first identified. This can be accomplished by routine experiment as described below, using one or more groups of animals (preferably at least 5 animals per group).

In animals, inhibition by pantethine treatment of hyperglycemia, glucose intolerance, insulin resistance and hyperinsulinemia can be assessed by administering the pantethine at a particular time of day and determining the effect of the administration (if any) by measuring one or more indices associated with glucose or insulin metabolism, and comparing the post-treatment values of these indices to the values of the same indices prior to treatment. Thus, glucose level, insulin level, insulin sensitivity or levels of glycosylated hemoglobin can be assayed using techniques that are well known to those skilled in the art. A convenient first time for administering pantethine is towards the beginning of the daily activity period of the host. The relevant metabolic indices are measured prior to, during, and after treatment.

If the time chosen is sufficiently effective in decreasing glucose or insulin metabolism indices, the experimentation can stop. If the results of the administration are not satisfactory, then the appropriate time of administration is adjusted as follows: The pantethine can be administered to the same (or preferably another) group of animals at a different time of day and the same indices can be measured, and compared to the first set of glucose or insulin index values and/or to a pretreatment set of glucose or insulin index variables. The second test time of administration is preferably 6–12 hours earlier (or later) than the first test administration time. Based on the difference in index values, the second test time can be selected as the time of therapy, or another (third) test time of administration can be selected by interpolation (or extrapolation). For example, if a third time were selected in Example 1 or 2 it could have been around 1400 h. At most, this time-ascertaining experiment would need to be conducted four times. The duration of each test treatment is 2–14 days.

In this manner a preferred effective time of administration for affecting glucose metabolism, i.e. a time of administration during the lipogenic metabolism responsiveness "window" or "interval" can be readily determined. The present inventors have also found that pantethine has more pronounced beneficial effects on aberrant glucose metabolism if administered at certain predetermined times during a 24-hour period. Again, a first test time of administration is selected and a test administration is conducted for 2–14 days. If the result is not satisfactory (based on comparison of the values of pre-treatment and post-treatment glucose metabolic indices) a second administration time is selected (and optionally a second group of animals is tested), and so on as described above.

If the treatment selected is effective, the time of the test administration is adopted as the time of treatment.

If the time selected is not sufficiently effective (i.e. produces no significant change, or produces an adverse change in the relevant metabolic parameter or parameters) then administration at this time is immediately discontinued and a different time is selected (6–12 hours before or after the first time). The test treatment and metabolic index measurement is then repeated.

It should be noted that the time of light onset and duration of daylight as well as the age, sex and physical condition and the activity/rest regimen of the subject to be treated will influence the time or times at which administration of pantethine will be effective. It is thus most preferred to ascertain an effective administration time for each individual, using the above-described method. This is particularly true of humans who have diverse daily timetables.

The amount of pantethine to be used depends in part on the duration of the increased glucose metabolism responsiveness interval or window.

The precise time of administration and/or amount of pantethine that will yield the most effective results in terms of efficacy of treatment in a given patient will depend upon the physiological condition of the patient (including age, sex, disease type and stage, general physical condition, responsiveness to a given dosage and type of medication) and the route of administration. However, the above guidelines can be used as the basis for fine-tuning the treatment, e.g., determining the optimum time and/or amount of administration, which will require no more than routine experimentation consisting of monitoring the subject and adjusting the dosage and/or timing.

While the subject is being treated, glucose metabolism is monitored by measuring one or more of the relevant indices at predetermined times during a 24-hour period. Treatment (amounts and times of administration) may be adjusted (optimized) according to the results of such monitoring. The patient (or other subject) is periodically reevaluated to determine extent of improvement by measuring the same parameters, the first such reevaluation typically occurring at the end of four weeks from the onset of therapy, and subsequent reevaluations occurring every 4 to 8 weeks during therapy and then every 3 months thereafter. Therapy may continue for several months or even years with six months to one year being a typical length of therapy for humans. Some patients (e.g. patients in particularly poor physical condition, or those of an advanced age) may require a longer, or even continuous, treatment with pantethine.

Adjustments to the amount of pantethine administered and possibly to the time of administration may be made based on these reevaluations. For example, if after 4 weeks of treatment one of the metabolic indices has not improved but at least one other index has, the dose could be increased by ⅓ without changing the time of administration.

Adjustments will be further modified and fine-tuned on an individual basis.

In most cases, adjustment of timing and amount of pantethine is not considered necessary if the results (i.e. amelioration of the metabolism disorder or disorders involved) are positive, i.e. if a clinically significant improvement has been achieved.

In treating non human vertebrates, generally, dosages within the aforementioned range of pantethine are given, typically over a period ranging from about 10 days to about 180 days. Longer treatment times are possible when a benefit is obtained.

In the practice of this invention, pantethine is administered daily to a subject preferably orally, or by subcutaneous, intravenous or intramuscular injection. Dermal delivery systems e.g., skin patches, as well as suppositories and other well-known systems for administration of pantethine can also be employed.

According to the invention timed administration of pantethine can also be employed to reduce body fat stores. In practicing this embodiment of the invention the same dosage and route of administration may be employed as for regulation of glucose metabolism.

LONG-TERM EFFECTS

Another aspect of the invention is directed to administration of pantethine to produce long-term, lasting, or even permanent effects on glucose metabolism by the administration of timed daily dosages to a vertebrate, animal or human, of pantethine. The dosages are continued on a daily basis for a period sufficient to cause the beneficial effects on glucose metabolism to persist. This amounts to resetting the phase of at least one major neuroendocrine circadian rhythm (e.g., the central neural oscillator expressed by the circadian rhythm of circulatory prolactin) in the subject being treated, in that the phase and amplitude of the prolactin rhythm is modified to resemble that for a healthy, lean, young subject of the same species (and, if applicable, of the same sex), i.e. moves closer to that depicted in FIG. 1. This change in phase and amplitude can be assessed by comparison of the pre-treatment prolactin values at various times of the day before and after treatment. (See, e.g., applications Ser. Nos. 07/995, 292 now U.S. Pat. No. 5,585,347 or 08/264,558 now abandoned.) The interval of increased glucogenesis of the subject can thus be related to the prolactin level daily rhythm of the subject. Essentially, any change in secretion, or blood level, of any hormone or other phenomenon which occurs in a circadian pattern and constitutes an expression of a central neural oscillation can be used to monitor alterations in the central neural oscillation it expresses.

Examples include prolactin, cortisol, thyrotropin, insulin, and body temperature without limitation. Resetting of circadian rhythms occurs if the administration of the pantethine (at a predetermined time) is continued for a period of time, generally at least about 10 days, preferably several months (e.g. typically 6 months for humans). Resetting has occurred if the beneficial effect(s) on the glucose metabolism persist on a long-term basis (e.g. months or even years) after the drug is discontinued. The foregoing amount, ranges and times of administration are the same as above. The doses of pantethine can be adjusted according to the results they produce in terms of the glucose metabolism indices as described above.

These and other features of the invention will be better understood by reference to the experiments described in the examples below. In the examples the terminology "LD" refers to the light/dark cycle, the first number following the expression LD refers to the hours of light, and the second to the hours of darkness in the cycle. Thus, LD 14:10 refers to a cycle having 14 hours of light and 10 hours of darkness, and the period of a day is expressed in terms of 2400 hours. "BW" designates body weight, g represents grams, and mg represents milligrams.

All reagents and materials are commercially available. It should be noted that the Syrian hamster is a good, reliable model for both obesity and insulin resistance conditions in humans.

EXAMPLE 1: SHORT-TERM EFFECTS OF PANTETHINE ON GLUCOSE METABOLISM IN SYRIAN HAMSTERS

Twenty-three female Syrian hamsters (Simonsen laboratories) which were 10 weeks old were separated into 4 groups of 5–6 hamsters each and placed on short daylengths (LD 10:14). Following 4 weeks of acclimation on short daylengths, 2 groups of hamsters were treated with pantethine (Sigma, St. Louis) by gavage, 55 mg per kg body weight in 1 ml tap water at either the onset or offset (0800 or 1800, respectively) of light. The other 2 groups served as controls and were given tap water by gavage at the two treatment times. After 25 days of treatment, glucose tolerance tests were performed by the method of Tzur et al. (1988) at 1 hour before the onset of light. Hamsters were lightly anesthetized with sodium pentobarbitol and injected intraperitoneally with a 50% solution of glucose (2.0 g per kg of body weight). Blood samples were taken from the external jugular vein before and at 30, 60, 90, and 120 minutes after glucose injection. Plasma glucose concentrations were determined enzymatically using glucose oxidase coupled with peroxidase (Sigma Diagnostics, St. Louis). Plasma insulin concentrations were determined by double-antibody radioimmunoassay utilizing radiolabelled porcine insulin, guinea pig antisera, and porcine insulin as standards (Binax, Portland, Oreg.) Plasma prolactin concentrations were determined by homologous double-antibody radioimmunoassay utilizing materials supplied by Frank Talamantes (University of California, Santa Cruz). The effects on glucose metabolism are shown in Table 1, below:

TABLE 1

|  |  | PANTETHINE | | CONTROL | |
| --- | --- | --- | --- | --- | --- |
| TIME POINT, n |  | 0800 n = 5 | 1800 n = 6 | 0800 n = 6 | 1800 n = 6 |
| Glucose Tolerance (AUC) | TOTAL | 222.1 ± 31.7* | 220.7 ± 40.3* | 514.1 ± 25.8 | 530.1 ± 124.9 |
|  | STIMULATED | 54.3 ± 15.9* | 27.5 ± 22.6* | 282.0 ± 38.8 | 278.3 ± 107.4 |
| INSULIN |  | 59.4 ± 13.1* | 70.6 ± 21.2* | 111.4 ± 22.1 | 124.8 ± 45.5 |
| GLUCOSE (mg/ml) |  | 103.9 ± 11.2 | 99.9 ± 14.7 | 125.1 ± 11.8 | 125.9 ± 16.4 |
| PROLACTIN (ng/ml) |  | 129.3 ± 27.5* | 99.7 ± 34.1* | 722.9 ± 165.8 | 301.8 ± 46.3 |

*Differs significantly from control (P < 0.01)
AUC = AREA UNDER CURVE

The experiment reported in this example was designed to test for the differences in the effectiveness of pantethine based on time of administration. Times were selected to target pantethine administration either toward (0800 h) or away (1800) from the peak interval of lipogenic and glycogenic activity in the healthy Syrian hamster. Pantethine treatment significantly reduced both total and stimulated areas under the glucose curve (glucose tolerance test, Table 1). Areas were reduced by 58% and 88%, respectively, in comparison to control groups. Both treatment times significantly reduced basal (time 0, before glucose injection) plasma insulin concentrations by an average of 45%. Plasma prolactin concentrations were also reduced (as measured at time 0) at both treatment times by 82%(0800) and 67% (1800).

EXAMPLE 2: LONG-TERM EFFECTS OF PANTETHINE TREATMENT ON GLUCOSE AND LIPID METABOLISM

Eleven weeks after cessation of pantethine treatment, blood samples were taken from the animals in the control and treatment groups described in Example 1 after a glucose administration as in Example 1 in order to obtain measurements of glucose metabolism and insulin concentrations. All measurements were made according to the methodologies described in Example 1. The animals were then sacrificed and measurements of their retroperitoneal fat stores were made by weighing. The results are shown in Table 2, below:

(27%, 0800; 67%, 1800). Basal insulin concentrations were also reduced approximately 60% (0800 and 1800 treatments combined). Pantethine treatment also markedly reduced retroperitoneal fat stores by an average of 31%; the 0800 treatment being significantly more effective at reducing retroperitoneal fat stores than the 1800 treatment time. The invention was described above with reference to preferred embodiments. In light of this description, however, it will be apparent to those skilled in the art that many omissions, additions and modifications are possible, all within the scope of the following claims.

What is claimed is:

1. A method for modifying glucose metabolism in a vertebrate animal or human subject in need of such treatment which comprises administering at a predetermined time of day to said animal or said human subject an effective mount of pantethine for modifying the glucose metabolism of said animal or said subject.

2. The method of claim 1 wherein said administration is effective to accomplish at least one of the following:
   i) decrease hyperglycemia;
   ii) decrease glucose intolerance;
   iii) decrease insulin resistance; and
   iv) decrease hyperinsulinemia.

3. The method of claim 1 wherein said subject is a human.

4. The method of claim 3 wherein said predetermined time is within the interval from about 07:00 h to 13:00 h.

5. The method of claim 3 wherein said effective amount is between about 15 and 500 mg per kg of body weight per day.

TABLE 2

|  |  | PANTETHINE | | CONTROL | |
| --- | --- | --- | --- | --- | --- |
| TIME POINT, n |  | 0800 n = 5 | 1800 n = 6 | 0800 n = 6 | 1800 n = 6 |
| Glucose Tolerance (AUC) | TOTAL | 357.6 ± 57.7* | 280.8 ± 62.1* | 413.4 ± 80.8 | 438.0 ± 59.3 |
|  | STIMULATED | 155.5 ± 37.8* | 96.3 ± 55.9* | 321.8 ± 57.1 | 315.9 ± 75.7 |
| INSULIN |  | 25.9 ± 5.1* | 39.0 ± 8.0 | 76.8 ± 35.1 | 83.4 ± 23.4 |
| GLUCOSE (mg/ml) |  | 101.4 ± 4.5 | 92.2 ± 4.9 | 114.7 ± 24.4 | 93.8 ± 7.6 |
| RETROPERITONEAL FAT STORES (g) |  | 5.5 ± 0.4*,b | 7.4 ± 0.7* | 8.0 ± 0.9 | 10.8 ± 0.6 |

*Differs significantly from control (P < 0.01)
bDiffers significantly from 1800 h treatment time (p < 0.01)
AUC = AREA UNDER CURVE Eleven weeks after cessation of treatment, the effects of pantethine treatment on indices of glucose metabolism were still evident (Table 2). Total and stimulated areas under the glucose tolerance test curve were significantly decreased 6. The method of claim 4 which comprises administering multiple doses of said pantethine within said time interval.

7. The method of claim 5 wherein said effective amount is between about 20 and about 350 mg per kg of body weight per day.

8. The method of claim 3 wherein said pantetheine is administered for between about 10 and about 180 days.

9. The method of claim 1 wherein said predetermined time is the beginning of the daily activity period for said animal or subject.

10. A method for correcting abnormalities in the glucose metabolism of a vertebrate animal or human subject in need of such treatment which comprises administering at a predetermined time of day to said animal or said subject an effective amount of pantethine, said administration being effective to accomplish at least one of the following:

i) decrease hyperglycemia;

ii) decrease glucose intolerance;

iii) decrease insulin resistance; and iv) decrease hyperinsulinemia.

11. The method of claim 10, wherein said subject is a human.

12. The method of claim 11 wherein said predetermined time is within the interval from about 07:00 h to 13:00 h.

13. The method of claim 11, wherein said pantetheine is administered for between about 10 and about 180 days.

14. The method of claim 10 wherein said effective amount is between about 15 and 500 mg/kg of body weight per day.

15. The method of claim 14 wherein said effective amount is between about 20 and about 350 mg/kg of body weight per day.

16. The method of claim 14 which comprises administering multiple doses of said pantetheine within the interval from about 07:00 h to 13:00 h.

17. The method of claim 10 wherein said subject is a human and said predetermined time is within the interval from about 07:00 h to 13:00 h.

18. The method of claim 10, wherein said predetermined time is the beginning of the daily activity period for said animal or subject.

19. A method for modifying glucose metabolism in a vertebrate animal or human subject in need of such treatment which comprises administering at a predetermined time of day to said animal or said human subject an effective amount of cysteamine for modifying the glucose metabolism of said animal or said human subject.

20. The method of claim 19 wherein said predetermined time is the beginning of the daily activity period for said animal or subject.

21. The method of claim 19 wherein said administration is effective to accomplish at least one of the following:

i) decrease hyperglycemia;

ii) decrease glucose intolerance;

iii) decrease insulin resistance; and iv) decrease hyperinsulinemia.

22. The method of claim 19 wherein said subject is a human.

23. The method of claim 22, wherein said predetermined time is within the interval from about 07:00 h to 13:00 h.

24. The method of claim 22, wherein said cysteamine is administered for between 10 and about 180 days.

25. The method of claim 24 which comprises administering multiple doses of said cysteamine within the interval from about 07:00 h to 13:00 h.

26. The method of claim 19 wherein said effective amount is between about 15 and about 500 mg/kg of body weight per day.

27. The method of claim 26, wherein said effective amount is between about 20 and about 350 mg/kg of body weight per day.

* * * * *